(12) United States Patent
Dassopoulos et al.

(10) Patent No.: US 11,666,286 B2
(45) Date of Patent: *Jun. 6, 2023

(54) CLASSIFICATION OF POLYPS USING LEARNED IMAGE ANALYSIS

(71) Applicants: BAYLOR RESEARCH INSTITUTE, Dallas, TX (US); WRIGHT STATE UNIVERSITY, Dayton, OH (US)

(72) Inventors: Themistocles Dassopoulos, Dallas, TX (US); Nikolaos Bourbakis, Dallas, TX (US)

(73) Assignees: BAYLOR RESEARCH INSTITUTE, Dallas, TX (US); WRIGHT STATE UNIVERSITY, Dayton, OH (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/305,105

(22) Filed: Jun. 30, 2021

(65) Prior Publication Data

US 2021/0397904 A1 Dec. 23, 2021

Related U.S. Application Data

(63) Continuation of application No. 16/339,921, filed as application No. PCT/US2017/055640 on Oct. 6, 2017, now Pat. No. 11,055,581.

(Continued)

(51) Int. Cl.
*G06T 7/00* (2017.01)
*G06T 11/00* (2006.01)
(Continued)

(52) U.S. Cl.
CPC .......... *A61B 5/7267* (2013.01); *G06F 16/583* (2019.01); *G06F 18/24317* (2023.01);
(Continued)

(58) Field of Classification Search
CPC ... G06K 9/6281; G06T 7/0014; G06T 11/001; G06T 2207/30004; G06V 10/143; G06V 10/82; G06V 10/16
See application file for complete search history.

(56) References Cited

U.S. PATENT DOCUMENTS 11,055,581 B2 * 7/2021 Dassopoulos ............ G06N 5/04
2004/0064029 A1 * 4/2004 Summers ................ G16H 15/00
600/407

(Continued)

OTHER PUBLICATIONS

Gross, et al., "Polyp Segmentation in NBI Colonoscopy," *Bildverarbeitung fur die Medizin 2009*. Mar. 2009. Retrieved from <https://pdfs.semanticscholar.org/f594/7d23080a3ea4173b18d0a31c82533232c2ee.pdf>.

(Continued)

*Primary Examiner* — Ming Y Hon
(74) *Attorney, Agent, or Firm* — Norton Rose Fulbright US LLP (57) ABSTRACT

Computational techniques are applied to video images of polyps to extract features and patterns from different perspectives of a polyp. The extracted features and patterns are synthesized using registration techniques to remove artifacts and noise, thereby generating improved images for the polyp. The generated images of each polyp can be used for training and testing purposes, where a machine learning system separates two types of polyps.

18 Claims, 5 Drawing Sheets

Related U.S. Application Data (60) Provisional application No. 62/405,625, filed on Oct. 7, 2016.

(51) Int. Cl.

| | | |
|---|---|---|
| *G06V 10/141* | (2022.01) | |
| *G06V 10/143* | (2022.01) | |
| *G06V 10/82* | (2022.01) | |
| *A61B 5/00* | (2006.01) | |
| *G16H 50/50* | (2018.01) | |
| *G16H 50/20* | (2018.01) | |
| *G16H 30/40* | (2018.01) | |
| *G06F 16/583* | (2019.01) | |
| *G06N 20/00* | (2019.01) | |
| *G06N 5/04* | (2023.01) | |
| *G06F 18/243* | (2023.01) | |
| *G06V 10/42* | (2022.01) | |
| *G06V 10/764* | (2022.01) | |
| *A61B 1/31* | (2006.01) | |
| *G06V 10/10* | (2022.01) | |

(52) U.S. Cl.
CPC ............... *G06N 5/04* (2013.01); *G06N 20/00* (2019.01); *G06T 7/0014* (2013.01); *G06T 11/001* (2013.01); *G06V 10/141* (2022.01); *G06V 10/143* (2022.01); *G06V 10/431* (2022.01); *G06V 10/764* (2022.01); *G06V 10/82* (2022.01); *G16H 30/40* (2018.01); *G16H 50/20* (2018.01); *G16H 50/50* (2018.01); *A61B 1/31* (2013.01); *G06T 2207/30004* (2013.01); *G06V 10/16* (2022.01); *G06V 2201/032* (2022.01)

(56) References Cited

U.S. PATENT DOCUMENTS

| | | | |
|---|---|---|---|
| 2005/0147284 A1 | 7/2005 | Vining et al. | |
| 2007/0276214 A1 | 11/2007 | Dachille et al. | |
| 2008/0058593 A1* | 3/2008 | Gu | G06T 5/40 |
| | | | 600/109 |
| 2010/0260390 A1 | 10/2010 | Liang et al. | |
| 2013/0012794 A1* | 1/2013 | Zeng | G01J 3/28 |
| | | | 600/179 |
| 2014/0099011 A1* | 4/2014 | Begin | G06T 5/002 |
| | | | 382/131 |
| 2018/0253839 A1* | 9/2018 | Zur | A61B 1/000095 |
| 2019/0080454 A1* | 3/2019 | Hameed | G01B 11/30 |

OTHER PUBLICATIONS

Hafner, et al., "Local Fractal Dimension Based Approaches for Colonic Polyp Classification," Medical Image Analysis, 1-20, Sep. 2, 2015, Retrieved from <http://wavelab.at/papers/Haefner15b.pdf>.

International Search Report and Written Opinion Issued in Corresponding PCT Application No. PCT/US2017/055640, dated Dec. 18, 2017.

Preim, et al., "A Survey of Perceptually Motivated 3D Visualization of Medical Image Data," *Computer Graphics Forum*, 35(3), May 2, 2016. Retrieved from <https://hal.inria.fr/hal-01310290/document>.

Wang, et al., "Seeing is Believing: Video Classification for Computed Tomographic Colonography Using Multiple-Instance Learning," IEEE Transactions on Medical Imaging, 31(5): 1141-1153, 2012. Retrieved from <https://www.ncbi.nlm.nih.gov/pmc/articles/PMC3480731/pdf/nihms409930.pdf>.

* cited by examiner

CLASSIFICATION OF POLYPS USING LEARNED IMAGE ANALYSIS

CROSS-REFERENCE TO RELATED APPLICATION

This application is continuation of U.S. Ser. No. 16/339,921, filed Apr. 5, 2019, which is a national phase under 35 U.S.C. § 371 of International Application No. PCT/US2017/055640, filed Oct. 6, 2017, which claims the benefit of U.S. Provisional Patent Application No. 62/405,625, entitled, "CLASSIFICATION OF POLYPS USING LEARNED IMAGE ANALYSIS," filed on Oct. 7, 2016, the disclosures of each of which are hereby incorporated by reference herein in their entirety as if fully set forth below and for all applicable purposes.

BACKGROUND

Over 14 million colonoscopies are performed annually in the United States, two thirds of which are performed to screen and survey for colorectal neoplasia. Diminutive polyps, which are defined as ≤5 mm in size, constitute 80% of all polyps found during a colonoscopy and can be classified as either (1) hyperplastic (i.e., benign), or (2) adenomatous (i.e., potentially precancerous). While the risk of cancer within such diminutive polyps is minimal, an assessment of the polyp's histology is important because it determines how often the polyp undergoes surveillance going forward. Also, for various reasons, diminutive polyps are more difficult to assess and/or classify than their larger counterparts. As a result, a histologic assessment of diminutive polyps accounts for a significant portion of costs associated with colon cancer screening.

If colonoscopies could accurately distinguish diminutive adenomatous polyps from diminutive hyperplastic polyps, then adenomatous polyps could be resected and discarded without pathologic confirmation (i.e., according to a "diagnose and discard" strategy), while hyperplastic polyps could be left in situ (i.e., according to a "diagnose and leave" strategy). This would significantly reduce pathology costs associated with screening. Additional benefits would include reducing the costs of polypectomy equipment, decreasing post-polypectomy complications, and allowing a pathologist to communicate a recommended colonoscopy surveillance interval to the patient immediately after the colonoscopy.

Consistent with the foregoing, being able to perform a real-time endoscopic prediction of the histology of polyps, especially, diminutive polyps, could save over one billion dollars per year in the U.S., while having a negligible impact on the accuracy of forward-looking surveillance and treatment protocols. Recognizing this potential benefit, the American Society of Gastrointestinal Endoscopy (ASGE) established performance benchmarks to allow adoption of a diagnostic technology into practice: (1) for diminutive polyps to be left in situ, the diagnostic technology should have a ≥90% negative predictive value (NPV) for adenomatous histology when used with high confidence; and (2) for diminutive polyps to be resected and discarded without pathologic assessment, the diagnostic technology (when used with high confidence and combined with the histopathological assessment of polyps>5 mm), should agree at least 90% of the time with the standard approach (which is based on the histologic assessment of all identified polyps).

SUMMARY

The classification of polyps using learned image analysis described herein can encompass one or more of the following aspects, features, implementations, and combinations. In one respect, a system for classifying polyps is disclosed. The system comprises an image database, which itself comprises, for a plurality of polyps, images of the plurality of polyps taken from different perspectives. In certain embodiments, the system is for classifying diminutive polyps, i.e. polyps that are 5 mm in size or less.

Importantly, the inventive concepts described herein provide several advantages over currently available technology. For example, a previously known approach for classifying polyps involves the use of Narrow Band Imaging (NBI) by endoscopists. However, several barriers prevent the wide implementation of NBI-based diagnosis by endoscopists. By way of example, NBI-based diagnosis performs well only under very specific circumstances, namely when an expert endoscopist is making a high-confidence assessment. However, not all expert or academic gastroenterologists meet the American Society of Gastrointestinal Endoscopy (ASGE) benchmarks. Moreover, under known methods such as standard NBI analysis, endoscopists will require training, certification, and periodic re-certification for NBI diagnosis. The development, maintenance, and oversight of quality assurance programs will require significant investments. Also, it remains to be seen whether community gastroenterologists can replicate and sustain in routine practice the ASGE performance benchmarks. In sum, existing approaches are expensive, time consuming, and cumbersome.

Embodiments described herein provide a technical solution to the foregoing limitations, such that automated analysis of NBI images can meet and exceed the ASGE performance benchmarks, and therefore constitute a high value innovation for the United States health care system. Inventive concepts overcome many of the deficiencies of known approaches by providing an integrated method embodied in computer software for use with a computer for a rapid, efficient, and cost efficient system for classifying polyps, for example, but not limited to diminutive polyps. In doing so, described embodiments provide a specific technical solution to the problem of classifying polyps that removes the requirement that an ASGE certified physician examine the images of the classified polyps. Essentially, the inventive concepts obviate the requirement that certain physicians (e.g., qualified physicians) review polyp images and/or classifications of polyps performed by other physicians. Instead, the system provides an automated process that removes the need for human evaluation.

The system comprises a polyp imaging engine, which is configured to compile, for at least one of the plurality of polyps, images of the at least one of the plurality of polyps taken from different perspectives. The polyp imaging engine is also configured to generate, from the compiled images of the at least one polyp, a new polyp image having fewer reflection artifacts and occlusions than the compiled images.

The polyp imaging engine is further configured to compute, based on the generated new polyp image, a polyp surface model.

The system further comprises a learning engine, which is configured to apply linear subspace learning techniques and nonlinear subspace learning techniques to identify discriminate features in the polyp surface model. The learning engine is also configured to, based on the identified discriminate features, apply specific rules to classify the polyp as adenomatous or hyperplastic. The types of rules applied by the learning engine can be set as initial default rules and modified at certain times based on system "learning." For example, the system can store classification of one or more polyps and compare the classification to the types of rules applied in arriving at that classification to better understand the accuracy and consistent of obtained results. Based on such comparisons, the learning engine can reinforce the application of the rules and/or modify the rules to obtain improved results. Application of these rules by the learning engine, rather than reliance upon a human for manually inspecting polyp images to arrive at a classification, is a notable improvement provided by the claimed invention.

In another respect, a method for classifying polyps is disclosed. The method comprises storing, in an image database, for a plurality of polyps, images of the plurality of polyps taken from different perspectives. The method also comprises compiling, for at least one of the plurality of polyps, images of at least one of the plurality of polyps taken from different perspectives. The method further comprises generating, from the compiled images of the at least one polyp, a new polyp image, the new polyp image having fewer reflection artifacts and occlusions than the compiled images. The method further comprises computing, based on the generated new polyp image, a polyp surface model. The method further comprises applying, by a learning engine, linear subspace learning techniques and nonlinear subspace learning techniques to identify discriminate features in the polyp surface model. The method further comprises classifying the polyp as adenomatous or hyperplastic based on the identified discriminate features.

DETAILED DESCRIPTION

Embodiments described herein provide for the classification of polyps using learned image analysis. More particularly, described embodiments utilize various novel features to create an improved system and method for classifying polyps in a clinical setting. Still further, the classification system and method is used to classify diminutive polyps in a clinical setting. The inventive concepts described herein provide several advantages over currently available technology. For example, a previously known approach for classifying polyps involves the use Narrow Band Imaging (NBI) techniques by endoscopists. However, without more, several barriers prevent the wide implementation of NBI-based diagnosis by endoscopists. By way of example, NBI-based diagnosis performs well only under very specific circumstances, namely when an expert endoscopist is making a high-confidence assessment. However, not all expert or academic gastroenterologists meet the American Society of Gastrointestinal Endoscopy (ASGE) benchmarks. Moreover, under known methods such as standard NBI analysis, endoscopists will require training, certification, and periodic re-certification for NBI diagnosis. The development, maintenance, and oversight of quality assurance programs will require significant investments. Also, it remains to be seen whether community gastroenterologists can replicate and sustain in routine practice the ASGE performance benchmarks. In sum, existing approaches are expensive, time consuming, and cumbersome.

Embodiments described herein provide a technical solution to the foregoing limitations, such that automated analysis of NBI images can meet and exceed the ASGE performance benchmarks, and therefore constitute a high value innovation for the United States health care system. Inventive concepts overcome many of the deficiencies of known approaches by providing an integrated method embodied in computer software for use with a computer for a rapid, efficient, and cost efficient system for classifying polyps, i.e., diminutive polyps. In doing so, described embodiments provide a specific technical solution to the problem of classifying polyps that removes the requirement that an ASGE certified physician examine the images of the classified polyps. Essentially, the inventive concepts obviate the requirement that certain physicians (e.g., qualified physicians) review polyps images and/or classifications of polyps performed by other physicians. Instead, the system provides an automated process that removes the need for human evaluation.

The system comprises a polyp imaging engine, which is configured to compile, for at least one of the plurality of polyps, images of the at least one of the plurality of polyps taken from different perspectives. The polyp imaging engine is also configured to generate, from the compiled images of the at least one polyp, a new polyp image having fewer reflection artifacts and occlusions than the compiled images. The polyp imaging engine is further configured to compute, based on the generated new polyp image, a polyp surface model.

The system further comprises a learning engine, which is configured to apply linear subspace learning techniques and nonlinear subspace learning techniques to identify discriminate features in the polyp surface model. The learning engine is also configured to, based on the identified discriminate features, apply specific rules to classify the polyp as adenomatous or hyperplastic. The types of rules applied by the learning engine can be set as initial default rules and modified at certain times based on system "learning." For example, the system can store classification of one or more polyps and compare the classification to the types of rules applied in arriving at that classification to better understand the accuracy and consistent of obtained results. Based on such comparisons, the learning engine can reinforce the application of the rules and/or modify the rules to obtain improved results. Application of these rules by the learning engine, rather than reliance upon a human for manually inspecting polyp images to arrive at a classification, is a notable improvement provided by the claimed invention.'

Aspects of described embodiments involve applying certain types of rules based on computational techniques to video images or individual images of polyps to extract features and patterns from different perspectives of a polyp. The extracted features and patterns are synthesized using registration techniques to remove artifacts and noise, thereby generating improved digital image data of a polyp. The generated images of each polyp can be used for training and testing purposes, where a machine learning system applies another set of rules and classifies polyps as one of two or more known types of polyps according to those rules, more specifically, known types of diminutive polyps.

Such embodiments utilize multiple images of diminutive polyps taken from different perspectives. As will be discussed in greater detail, the images are preferably generated from narrow band imaging (NBI) techniques. Using NBI, a diminutive polyp is illuminated at, e.g., 415 nanometers (nm) and 540 nanometers (nm), which are both strongly absorbed by hemoglobin. NBI techniques rely upon greater vascularity of adenomatous polyps to differentiate them from hyperplastic polyps. Multiple polyp views may be extracted from several separate images, or a video file obtained for the diminutive polyp.

Being able to utilize multiple perspectives of a polyp allows the system to generate new, "clean" polyp images with reduced reflection artifacts and occlusions. That is, according to embodiments, digital data from each the images taken from different perspectives can be compiled or otherwise combined to generate a composite digital image of a polyp. The composite digital image generated from the images taken from different perspectives has fewer reflection artifacts and occlusions than the compiled images. This allows computation of a refined polyp surface model not previously achievable. For example, using these techniques enables polyp's color, texture, size and multi-dimensional shape to be examined for classification purposes. These features can be extracted as, e.g., a set or individually, and mapped to feature sets or individual features of known polyp types for classification. In sum, obtaining improved images in this manner provides more information about the polyp surface and the like, allowing certain rules or certain types of rules to be applied by the learning engine in an automated fashion, which was simply not possible under known approaches. For instance, embodiments leverage the improved polyp images, and specifically the refined surface model generated in the composite image, to more efficiently apply linear and nonlinear subspace learning techniques to select the discriminant features that separate adenomatous from hyperplastic polyps.

Digital image data and/or clinical data relating to diminutive polyps obtained from one or more patients is input into the classification system, which filters the digital data and extracts salient features of the polyps. The feature extraction can occur at two stages. First, polyp features can be extracted and their respective extractions stored in a database when the database is populated with an initial set of polyp digital image data and clinical data. Data used to initially populate the database can be generated from polyps taken from screened patients and/or historical logs of such data. Second, polyp features can be subsequently extracted by operators at central or remote locations to update the system and/or perform comparisons to enable the classification process.

The subsequently extracted polyp features can be compared to the previously extracted polyp features and/or clinical data used to initially populate the database. That is, the extracted features are compared or mapped to polyp digital image data and/or clinical data stored in a database. Based upon the comparison or mapping, the polyps are classified as either neoplastic or non-neoplastic. A polyp is further classified where, if determined to be neoplastic, it is classified as benign (i.e., adenoma) or malignant (i.e., adenocarcinoma). If a polyp is determined to be non-neoplastic, it is further classified as normal mucosa, hyperplastic, lipoma, or the like. As discussed, these classifications determine the forward-looking treatment and surveillance protocol for a patient having the classified polyp.

According to certain aspects, embodiments are trained over a large, balanced set of polyps (i.e., a set of polyps that includes approximately the same number of polyps known to be of a first type (e.g., adenomatous polyps) and polyps known to be of a second type (e.g., hyperplastic polyps)). These aspects result in improved and robust classification performance in the clinical setting that meets or exceeds the ASGE performance benchmarks without the need for training operators. That is, the automated analysis of polyps, as described herein, has the potential of bypassing the limitation of endoscopist performance. Accordingly, described embodiments can achieve drastic cost savings for health care systems.

Figure 1:
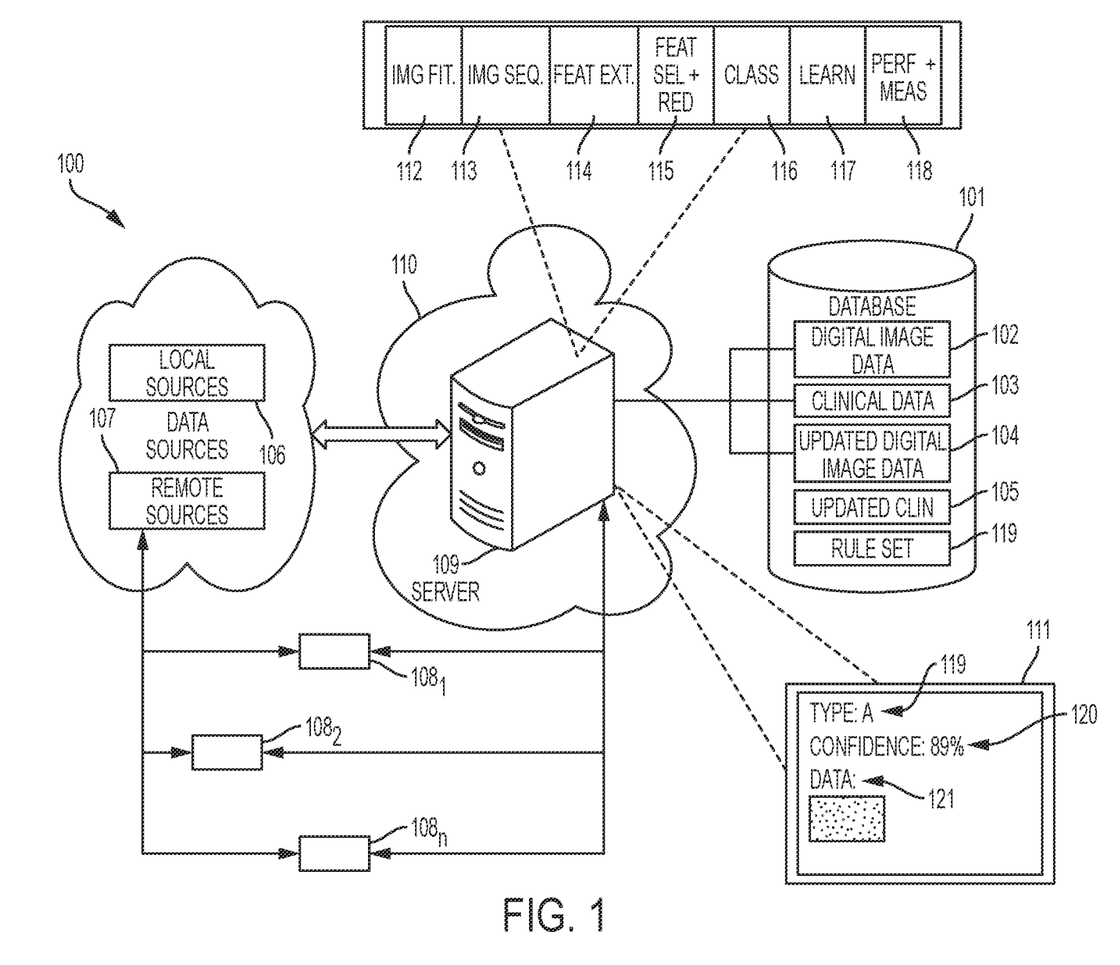
FIG. 1 is a block diagram illustrating certain aspects of embodiments disclosed herein.

FIG. 1 illustrates exemplary system 100 for classifying polyps based on a learned analysis of polyp images and assigning a confidence score to the classification of the polyp. Database 101 stores polyp digital image data and/or related digital clinical data. Database 101 can also store rules or sets of rules applied in the automated classification processes described herein. Again, the a combined order of rules can be applied that renders information into a specific format that is used and applied to create desired results, i.e., a meaningful classification of polyps without the need for human intervention.

The polyp digital image data may comprise white light (WL) and narrow-band image (NBI) data relating to polyps obtained from screened patients. The digital clinical data can comprise endoscopic reports, which can include data such as the colonoscopy indication, polyp size and location, the endoscopist's prediction of histology, etc. Digital clinical data can also comprise patient demographic information (e.g., age, gender), pathology report information, and the endoscopist's recommendation for future surveillance intervals.

Database 101 can be populated with an initial set of polyp digital image data 102 and clinical data 103, which can be compared to subsequently-received or updated polyp digital image 104 and/or subsequently-received or updated clinical data 105 to classify polyps depicted in subsequently-received polyp image data 104. Consistent with the foregoing disclosure, an initial set of digital image data 102 and clinical data 103 for a given polyp can comprise (a) WL and NBI endoscopic images of the polyp, (b) endoscopic reports (colonoscopy indications, polyp size and location, endoscopist's prediction of histology, etc.), (c) patient demographics (e.g., age, gender), (d) pathology reports, and (e) the endoscopist's recommendation for future surveillance intervals.

Database 101 can receive polyp image data 102 and 104 from various data sources, and can store clinical data 103 and 105, attribute data, mapping rules, classification types, and the like. Polyp digital image data and clinical data can be collected for polyps from screened patients and received from one or more local data sources 106 (e.g., an operator station local to server 109). Otherwise, digital image data stored in database 101 can be received from various remote data sources 107, e.g., such one of remote clinical operating stations (OS) 1081-108$n$. Remote data sources 107 can also include third party sources, online resources, and the like.

Database 101 can communicate various sets of digital image data 102 and 104 and clinical data 103 and 105, including feature extractions/feature extraction sets and rules for mapping the extracted features, to a server, e.g., server 109, that can be accessed from different nodes in network 110. Database 101 communicates with server 109, network 110 user interfaces at local clinical operating station (OS) 111, remote users operation stations 1081-108$n$, and other system components to effectuate automated classification of polyps as descried herein. This enables both local and remote system operators to access information for classification processes.

Consistent with the foregoing, database 101 is initially populated and/or updated before and during the classification steps described herein. According to an embodiment, database 101 is initially populated with image data 102 and clinical data 103 relating to one-thousand (1,000) polyps. The initial set of polyps ideally includes approximately the same number of different polyp types. Such a balanced set is thought to best enable subsequent learning steps to most efficiently classify polyps according to subsequently-received polyp image data.

Database 101 is also initially populated with rule sets 119, which establish what rules will be applied, and the order in which they will be applied, during the classification process. Rule sets 119 can specify, e.g., what extracted features will be used to perform a classification, the weight or priority the extracted feature will be given in the classification process, what features will be excluded or be classified as contrary to certain classifications, and the like. Rule sets 119 can also define how certain extracted features will be mapped during the classification process, as well as what combination of features will dictate a certain classification. Rules 119 can vary over time according to the learning techniques further described herein.

Once database 101 is populated with initial sets of polyp digital data, system 100 can construct improved digital images of polyps. The digital information is further processed by utilizing machine learning techniques to identify and extract relevant features from the digital image data. Learning techniques are further used to map the extracted features to data stored in database 101, according to rules 119 populated in and/or generated by the learning system, for purposes of comparison. Based on the comparison, polyps can be classified to accurately predict polyp histology. The mapping results and/or comparison results can be generated and displayed at user interface at one or more of OS 108 and/or OS 111. This obviates the need for manual assessment performed by an endoscopist.

Consistent with the foregoing, server 109 executes the steps described herein to effectuate polyp classification and measure the performance of system 100 against ASGE benchmark criteria. As one of skill in the art would understand, the components of server 109, whether hardware or software, may be collocated or distributed, e.g., across network 110. Server 109 comprises one or more functional blocks to execute the steps described herein. According to the illustrated embodiment, server 109 comprises image filter block 112, image segmentation block 113, synthesis and feature extraction block 114, feature selection and reduction block 115, classification block 116, learning block 117, and performance benchmark block 118.

Image filter block 112 operates to remove noise in polyp digital image data. In some instances, a number of polyp images may be unduly noisy, thereby affecting the subspace learning performance. In those instances, additional views of the polyp are generated by applying elastic registration between the acquired polyp views with varying smoothness regularization degrees. This technique is effective because it is largely insensitive to sample size issues.

Image segmentation block 113 operates to separate polyp digital image data into meaningful segments for further analysis. Feature extraction block 114 operates to extract salient features from the filtered and segmented polyp digital image data. In doing so, block 114 operates to generate local-global graphs based on attributes for an accurate representation of features that can be used to associate polyp features by creating multi-dimensional profiles. Advantageously, according to disclosed embodiments, the extracted features can provide information indicative of color, texture, and vascularity. A variety of color-based and texture-based features can be extracted. For instance, extracted features can include (1) Color Layout Descriptor, (2) Edge Histogram Descriptor, (3) Color and Edge Directivity Descriptor, (4) Fuzzy Color and Texture Histogram Descriptor, (5) Gabor filter descriptor, (6) Gray Level Co-Occurrence Matrices (Haralick features), (7) Tamura's texture features, (8) Edge Frequency descriptor, (9) Autocorrelation feature, (10) Primitive length feature, (11) size. Such features can be calculated over the ROI using the input image (WL or NBI) and its corresponding binary mask.

The extracted features are then reduced for selection in the classification process at block 115. The reduction process can be accomplished, at least in part, by applying rule sets 119 to the extracted features. For example, some features, according to rules 119, may be determined to be of little or no value in making a classification. Further, rules 119 may dictate that certain extracted features are an anomaly or otherwise contrary or unhelpful in arriving at a classification. That is, some features may be determined to be more harmful than helpful in the classification process. Other times, certain extracted features may be stored for later analysis and considered at a later time perhaps, e.g., after a preliminary classification has been made. In this way, certain extracted features may be used to check or otherwise scrutinize classifications. Certain extracted features may also be discarded and tagged for use once rules 119 are updated or otherwise modified to better consider the extracted features.

Classification block 116 selects the features that are mapped to polyp digital image data stored in database 101 according to learning rules stored in learning block 117. Learning block 117 provides subspace learning (SL) strategies to (1) identify and select feature spaces relevant to polyp classification, and (2) learn new features during the experimentation and real use. Therefore, embodiments of system 100 can utilize endoscopic images of a polyp (NBI and/or WL) as input, extract color and texture features, and classify it as a adenomatous or non-adenomatous by applying learning techniques to compared extracted features of the polyp from digital data.

Performance measurement block 118 measure the classification performance of system 100 against ASGE benchmarks ASGE benchmark information can be loaded into database 101 and/or server 109 for comparison with classification data output by system 100. To ensure that system 100 exceeds ASGE benchmark requirements, block 118 measures (a) the negative predictive value (NPV) for adenomatous histology of rectosigmoid polyps and (b) the agreement between the system-based and the standard, pathology-based recommendations for the post-polypectomy surveillance interval. In the event system 100 does not meet or exceed the ASGE benchmarks, it may transmit an alert to one or more clinical operator stations and/or via their respective user interfaces. Further, block 118 can communicate with other components to determine what learning algorithms, if any, should be updated to ensure compliance with the benchmarks.

Server 109 can receive polyp image data from data sources 106 and 107, either directly or via database 101. Data sources include local data sources 106 (e.g., clinical stations local to server 109) and remote data sources 107 (e.g., e.g., one of clinical stations 1081-108n. Remote stations 1081-108n can be clinical stations located in a part of the country or world different from server 109.

Server 109 acquires and analyzes polyp image data received from local data sources 106 and remote data sources 107, assigns classification 119 to the imaged polyps, and in some instances, assigns confidence score 120 to classification 119. The polyps can be categorized as neoplastic or non-neoplastic with a varying degree of confidence. Confidence score 120, as well as classification 119, can change over time as, e.g., server 109 iteratively applies the learning-based classification methods to received image data and updates to previously assigned classifications 119 and/or confidence scores 120 based on the newly-learned methods. For example, server 109 can select a subset of polyp digital image data 104 received from data sources 106 and 107, identify certain characteristics or features of image data 104, and map the identified characteristics or features to a certain polyp classification. This can be done with a degree of confidence 120.

Server 109 can store all or a portion of the received polyp image data in database 101. For example, server 109 can store image metadata 121, including image identification names and numbers, and the like, polyp classification 119, and confidence scores 120 in database 101, where each of confidence scores 120 corresponds with one of the available classifications 119 of the polyps in an image.

Confidence scores 120 may represent the confidence of polyp classification 119 for a polyp in a given image. For example, each of confidence scores 120 may represent the confidence of server 109 in the classification itself. Server 109 may use the appropriate methods and underlying algorithms (as described herein) to determine polyp classification 119 and the corresponding confidence scores 120, or other values that represent the strength of the classification itself.

An entity may use polyp classification 119 and the corresponding confidence scores 120 to classify a given polyp as one of a designated type of polyp. Based on that classification, and perhaps considering the confidence of that classification, the entity can make important decisions regarding how the polyp will be treated on a forward-looking basis. For example, the classification can determine the interval at which a patient is screened, the polyp is monitored, and/or how the polyp is treated at the time of classification. For example if a polyp is determined to be a of a first type of polyp with sufficient confidence, it may be left in situ. However, if the polyp is determined to be a second type of polyp with sufficient confidence, it may be removed without further biopsy or further pathological assessment (i.e., a discard protocol).

If the entity determines that the polyp is classified with a low confidence score and/or that additional image data is available with respect to the polyp, the entity can determine steps necessary to improve the confidence of the polyp's classification. Server 109 can analyze the newly-available or previously unconsidered image to update confidence score 120. If a change in confidence score 120 is made, the change can be updated accordingly in database 101 for later use by the entity.

In some implementations, server 109 includes database 101. For example, database 101 can be stored in a memory included in server 109. In some implementations, database 101 is stored in a memory on a device separate from server 109. For example, a first computer may include server 109 and a second, different computer may include the memory that stores database 101. In some implementations, database 101 may be distributed across multiple computers. For example, a portion of database 101 may be stored on memory devices that are included in multiple computers.

In some implementations, server 109 stores data received from the data sources 104 in memory. For example, server 109 may store data received from data sources 104 in database 101 or in another database.

Figure 2:
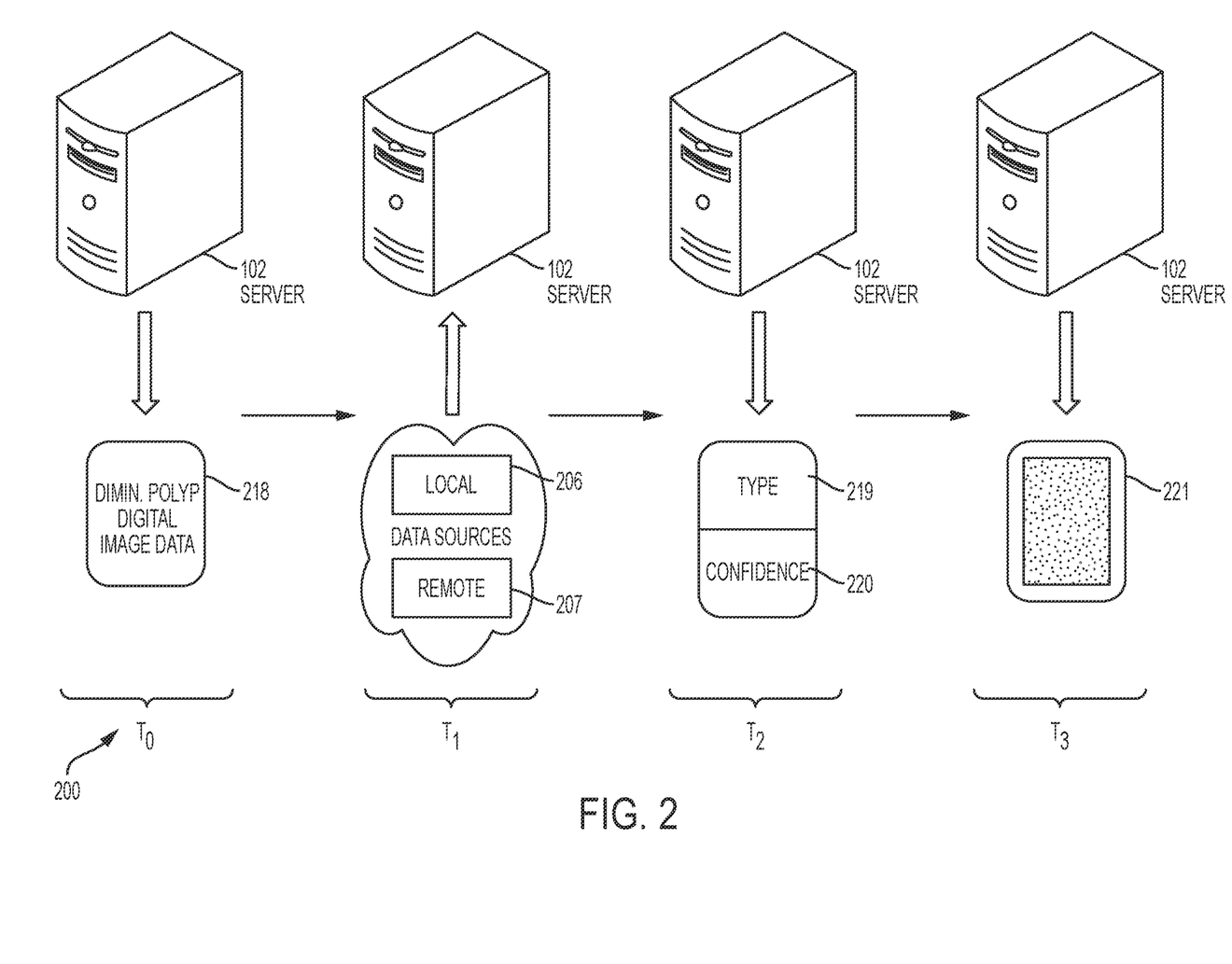
FIG. 2 is a is a block diagram illustrating certain aspects of embodiments disclosed herein.

FIG. 2 illustrates exemplary system 200 that assigns a classification (e.g., neoplastic or non-neoplastic) to a polyp and, in some implementations, also assigns a confidence score 220 to the classification 219. For example, during time To server 209 identifies one or more polyp images 218, or images 218 are identified by a user of system 200, for which server 209 will determine a classification and, in some implementations, a corresponding confidence score.

When, for example, a user is interested in classifying one or more newly-imaged diminutive polyps, the user can identify one or more polyp images 218 and instruct server 209 to classify a polyp depicted in identified images 218. When, for example, server 209 is performing a learning process or otherwise updating classifications 219 and/or confidence scores 220 for polyps depicted in images 218 (which may be newly received from image data sources 206 or 207 and/or previously stored in database 201), server 209 can identify (1) one or more polyp images 218 that are not currently assigned a particular classification 219, or (2) one or more diminutive polyp images 218 that were previously assigned a particular classification 219 and/or confidence score 220.

Server 209 can also identify one or more polyp images 218 that were assigned a previous classification 219 when new or updated data for those images are received. New or updated data can include new learning method rules that apply to the one or more images 218, data relating to the patient for which the images were made, data relating to the polyp depicted in the images, and the like. Server 209 can further identify one or more polyp images 218 based on a request for an updated classification 219 and/or confidence score 220, e.g., from a user of system 200. In the example shown in FIG. 2, server 209 has identified polyp image 218 that is not currently assigned a classification 219 or confidence score 220.

During time T1, server 209 receives image data from one or more image data sources 206 or 207, including newly-received polyp image 218 and/or new or updated data relating to a previously-stored polyp image 218. For example, server 209 identifies a subset of the received image data that is associated with image 218, where the subset of received image data will be analyzed to classify a polyp depicted in image 218. As described herein, image(s) 218 can be processed using NBI techniques. Server 209 can apply an evolving set of "learned" rules to the subset of received image data to generate classification 219 of the polyp depicted in image 218 that is more precise or refined than what would otherwise be available. In some instances, server 209 can apply the evolving set of "learned" rules to the subset of received image data to establish or update a confidence score 220 corresponding to classification 219.

The duration of the time period T1 may be any length of time. For example, the time period T1 may have a duration of seconds, minutes, or days. As other examples, the time period T1 may be months or years long. Note that, although the time periods shown in FIG. 2 do not overlap, in some cases they can overlap for any one or more polyp images 218.

Server 209, during time T2, maps the subset of image data, or image data of interest, associated with image 218 to attributes 221 associated with one or more classifications of polyps. The duration of the time period T2 may be any length of time. For example, the time period T2 may have a duration of seconds, minutes, or days. As other examples, the time period T2 may be months or years long.

As discussed in more detail herein, the subset of image data or image data of interest includes polyp features or feature sets that correspond to, are indicative of, or associated with one or more known polyp types. For example, when server 209 determines that the image data of interest includes feature sets associated with one or more polyp types, it can weight or rank the feature set to determine which of the one or more polyp types is most likely identified in the image data of interest. Based on the weight or rank, polyp image 218 can be assigned the most likely classification 219, and in some instances, a confidence score 220 associated with the classification.

In some implementations, as server 209 analyzes polyp image data in image 218, if server 209 identifies one or more attributes 221 or other features (which may comprise a feature set) and determines the one or more attributes 221 or features is associated with one or more particular types of polyp classifications, server 209 maps the one or more attributes 221 or features to a polyp classification. For example, server 209 can automatically map data to a "type 1" attribute based on image data and then automatically map data to a "type 2" attribute. In some examples, server 209 may update one or more attributes 221 as server 209 receives additional data associated with one or more polyp classifications. As server 209 receives additional information relating to the one or more polyp classifications, it can update its analysis of the one or more attributes 221, and determine if the one or more attributes should be re-mapped to a different polyp classification.

Server 209 may use some or all of attributes 221 of a polyp in image 218 to determine confidence score 221 of polyp classification 219. For example, server 209 may use color, texture, vascularity, etc., as one factor to determine confidence score 220 of polyp classification 219 of an identified polyp in image 218. Further, in some examples, server 209 may determine weights for attributes 221, where the weights represent the influence of the corresponding attribute 221 on confidence score 220.

For example, some attributes 221 may be viewed as strongly indicative, moderate indicative, or weakly indicative of a certain polyp classification. If a polyp in image 218 is determined to have one or more attributes 221 that are strongly initiate of a certain polyp type, confidence score 220 will likely be relatively high when classifying a polyp in image 218 as that particular type of polyp Also, in some implementations, the weights may vary based on intrinsic properties of attributes 220 and/or information relating to attributes 221. For example, if little information is available relating to the correlation between an attribute 221 and particular polyp classification, a confidence score based solely on such an attribute 221 would be relatively low. If, on the other hand, there is known to be a strong correlation between the presence of an attribute 221 and a particular polyp classification, a confidence score based on such an attribute 220 would be relatively high.

In some implementations, as mentioned earlier, one or more of the time periods T0, T1, T2, and T3 may overlap. For example, server 209 may request data from data sources 206 or 207, receive some of the requested data during time T1, identify one or more polyp images 218 during time T0, and then receive more of the requested data during time T1. In some examples, server 209 may map some of the requested data to a polyp attribute 221 during time T2 and while continuing to receive data from data sources 204 during time T1. In some examples, server 209 may determine confidence scores 220 for a polyp during time T3 while continuing to receive data from data sources 204 during time T1 and mapping the received data to one or more polyp attributes 220 during time T2.

In some implementations, server 209 can perform classification of a polyp in image 218, determining classification 219 and confidence score 220, in response to a request received from a third party. Also, in some implementations, server 209 can perform classification of a polyp in image 218, determining classification 219 and confidence score 220, automatically. For example, server 209 may determine that it has received more than a predetermined threshold quantity of data for a given polyp and that it should analyze the data to determine classification 219 and confidence score 220. Further, in some implementations, an operator of server 209 can identify which images 218 should be analyzed. For example, the operator can provide server 209 with a list images 218 for which server 209 should determine classifications 219 and confidence scores 220.

Figure 3:
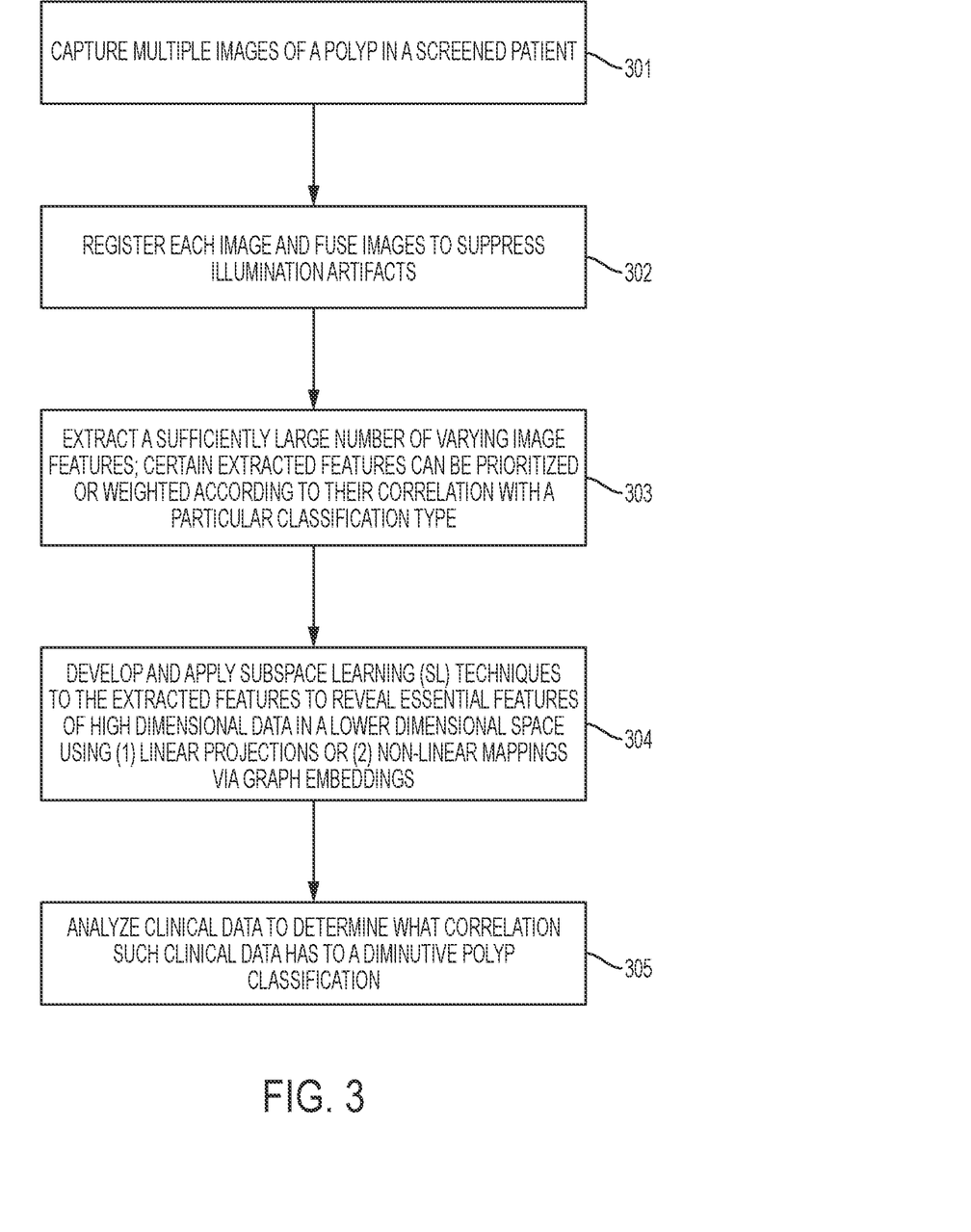
FIG. 3 is a flow chart diagram illustrating certain aspects of embodiments disclosed herein.

FIG. 3 is a flow chart that illustrates steps performed to classify polyps according to aspects of the present disclosure using, e.g., system 100 illustrated at FIG. 1. At step 301, multiple images are captured from a polyp in a screened patient. The multiple images are intentionally captured from different perspectives. Capturing polyp images from multiple perspectives decreases bad quality images (e.g., images subject to reflections, shadows, and the like), while increasing useable data. In one embodiment, multiple views of a polyp are captured using high-resolution, short videos of each polyp. This avoids the tedious task of capturing individual images. Collecting and using multiple views of the same polyp decreases images of low quality (i.e., images with reflections, shadows, etc.) while increasing useable input information. According to one embodiment, to capture multiple views, the system or the user can record high-resolution short videos of each polyp, thus avoiding the tedious task of taking individual images.

At step 302, each image is registered then fused to suppress illumination artifacts.

At step 303, a sufficiently large number of varying image features are extracted. Various discriminant polyp features, including color and texture, are extracted. This represents an improvement over known systems, which only select "good" features for extraction. Selecting a variety of features allows each feature to be measured with respect to its correspondence to a particular classification type. With that in mind, certain extracted features can be prioritized or weighted according to their correlation with a particular classification type.

At step 304, subspace learning (SL) techniques are developed and applied to the extracted features. This represents a key innovation that enables revealing the essential features of high dimensional data in a lower dimensional space by linear projections, or by non-linear mappings via graph embedding. Most SL methods compute directly the statistics of original training samples to learn the subspace. A dictionary is learned from the training dataset, and is used to sparsely decompose the training samples. This analysis forms a bio-inspired sparse representation of information, also known as sparse coding. Under varying illumination and occlusion conditions, embodiments create sparse representations using SL to build representations of the polyps that are not affected by imaging artifacts and occlusion. These representations will be used to estimate accurate decision functions and explore the separation between statistical prototypes of adenomas and non-adenomas.

In view of the foregoing, according to an embodiment, a SL technique are used for purposes of image recognition and to (1) reveal essential features of high dimensional data in a lower dimensional space using (1) linear projections, or (2) non-linear mappings via graph embeddings. SL techniques utilized by certain embodiments directly compute the statistics of original training samples to learn the subspace. A dictionary is learned from the training dataset, and is used to sparsely decompose the training samples. This analysis forms a bio-inspired sparse representation of information, which can also be referred to as sparse coding. Accordingly, SL techniques are used to construct representations of polyps that are not affected by imaging artifacts and occlusions. These representations will be used to estimate accurate decision functions and explore the separation between statistical prototypes of adenomas and non-adenomas.

At step 305, clinical data is also analyzed to determine what correlation such clinical data has to a polyp classification. Embodiments can utilize discriminant analysis to determine whether clinical data (e.g., patient age, polyp size and location, etc.) can improve the accuracy of the classification system.

Figure 4:
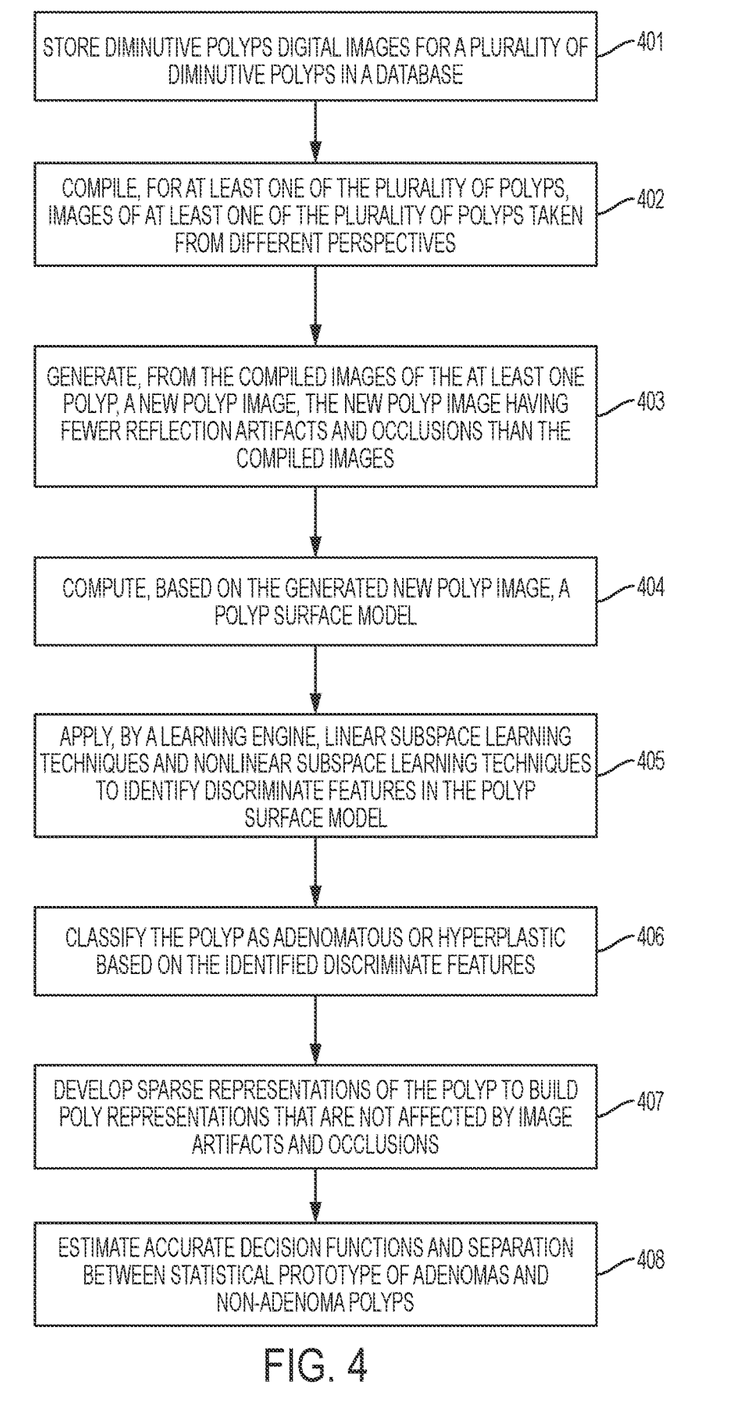
FIG. 4 is a is flow chart illustrating certain aspects of embodiments disclosed herein.

FIG. 4 is a flow chart that illustrates steps performed to classify polyps according to other aspects of the present disclosure using, e.g., system 100 illustrated at FIG. 1. At step 401, polyps digital image data is stored in a database. Specifically, step 401 comprises storing, in an image database, for a plurality of polyps, images of the plurality of polyps taken from different perspectives. Step 402 comprises compiling, for at least one of the plurality of polyps, images of at least one of the plurality of polyps taken from different perspectives.

Step 403 comprises generating, from the compiled images of the at least one polyp, a new polyp image, the new polyp image having fewer reflection artifacts and occlusions than the compiled images. In some embodiments, the images of the plurality of polyps taken from different perspective are generated using Narrow Band Imaging (NBI). This can be done by (1) generating a first image of at least one of the plurality of polyps using a light source emitting at or about 415 nanometers, and (2) generating a second image of the at least one of the plurality of polyps using a light source emitting at or about 540 nanometers. In other embodiments, the images of the plurality of polyps taken from different perspective are generated using a white light (WL) source.

Step 404 comprises computing, based on the generated new polyp image, a polyp surface model.

Step 405 comprises applying, by a learning engine, a linear subspace learning techniques and nonlinear subspace learning techniques to identify discriminate features in the polyp surface model. In some embodiments, color and/or texture data for images of at least one of the plurality of polyps taken from different perspectives is used as one or more discriminate features.

Step 406 comprises classifying the polyp as adenomatous or hyperplastic based on the identified discriminate features.

Step 407 comprises developing sparse representations of the polyp to build polyp representations that are not affected by imagine artifacts and occlusions.

Step 408 comprises estimating accurate decision functions and separation between statistical prototype of adenomas and non-adenomas polyps.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Figure 5:
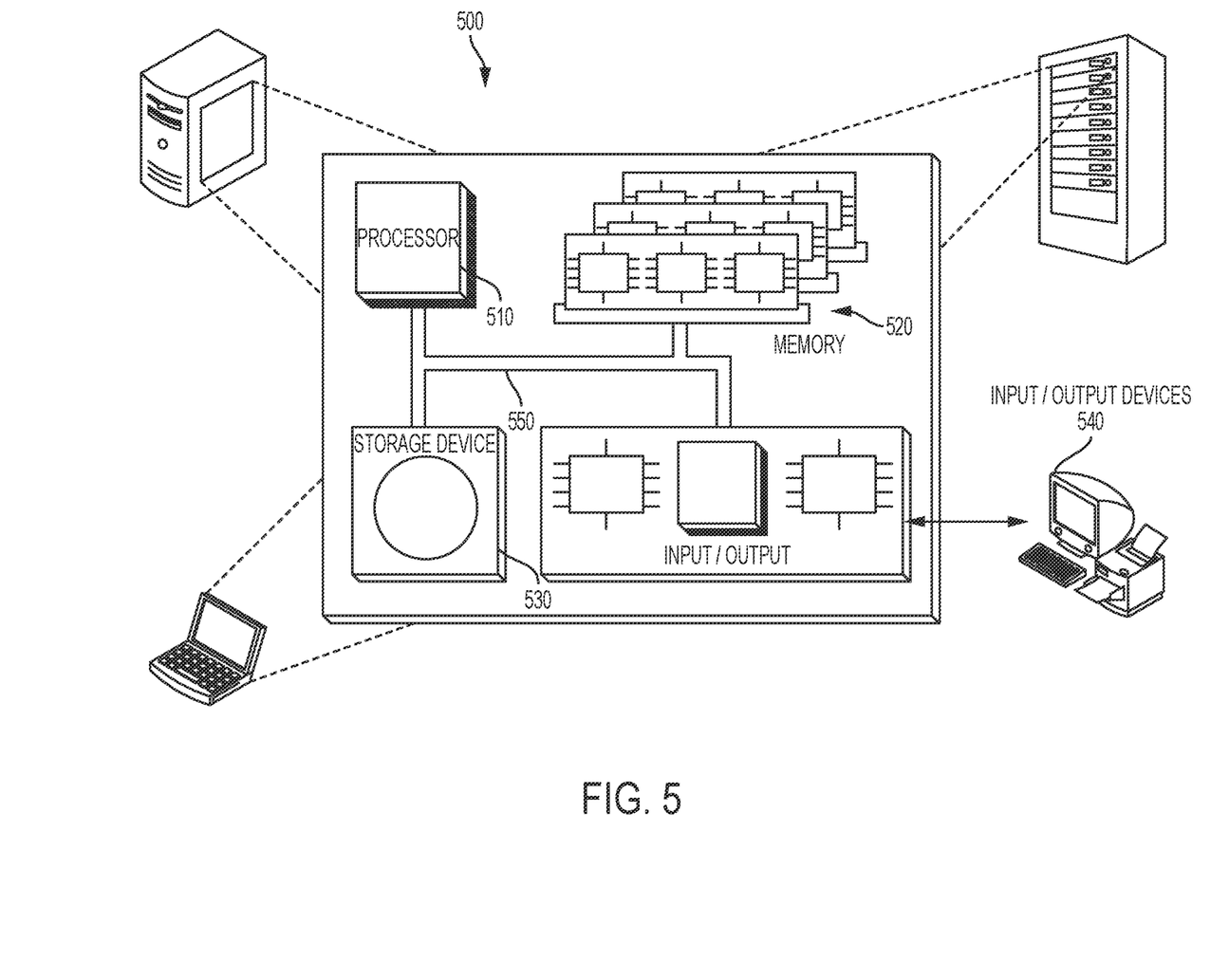
FIG. 5 is a is a block diagram illustrating certain aspects of embodiments disclosed herein.

FIG. 5 is a block diagram of an example computer system 500. For example, referring to FIG. 1, the automated polyp classification system 100 or a server forming a portion of the analysis system 100 could be an example of system 500 described here, as could a computer system used by any of the users who access resources of same. System 500 includes a processor 510, a memory 520, a storage device 530, and an input/output device 540. Each of components 510, 520, 530, and 540 can be interconnected, for example, using system bus 550. Processor 510 is capable of processing instructions for execution within system 500. In some implementations, processor 510 is a single-threaded processor. In some implementations, processor 510 is a multi-threaded processor. In some implementations, processor 510 is a quantum computer. Processor 510 is capable of processing instructions stored in memory 520 or on storage device 530. Processor 510 may execute operations such as the steps described above in reference to the process 300 (FIG. 3) or process 400 (FIG. 4).

Memory 520 stores information within system 500. In some implementations, memory 520 is a computer-readable medium. In some implementations, memory 520 is a volatile memory unit. In other implementations, memory 520 is a non-volatile memory unit.

Storage device 530 is capable of providing mass storage for system 500. In some implementations, storage device 530 is a computer-readable medium. In various different implementations, t storage device 530 can include, for example, a hard disk device, an optical disk device, a solid-date drive, a flash drive, magnetic tape, or some other large capacity storage device. In some implementations, storage device 530 may be a cloud storage device, e.g., a logical storage device including multiple physical storage devices distributed on a network and accessed using a network. In some examples, storage device 530 may store long-term data. Input/output device 540 provides input/output operations for system 500. In some implementations, input/output device 540 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. A network interface device allows system 500 to communicate, for example, transmit and receive data such as data from data sources 106 and 107 shown in FIG. 1. In some implementations, the input/output device can include driver devices configured to receive input data and send output data to other input/output devices, e.g., keyboard, printer and display devices at OS 111 and OS 108 in FIG. 1. In some implementations, mobile computing devices, mobile communication devices, and other devices can be used.

A server (e.g., a server forming a portion of the analysis system 109 shown in FIG. 1) can be realized by instructions that upon execution cause one or more processing devices to carry out the processes and functions described above, for example, storing data 102-105 in database 101 and assigning classifications 119 with confidence scores 120 (FIG. 1). Such instructions can include, for example, interpreted instructions such as script instructions, or executable code, or other instructions stored in a computer readable medium. A server can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

According to an embodiment, an interactive tool can be presented to a user via, e.g., a Graphical User Interface, that presents classification information and steps or instructions to execute based on the classification information. In some respects, the steps or instructions can be automated for execution by the system, or manual for execution by the user. The user can use the tool to provide feedback to the system such that the system continues to learn and provide refined feedback at a later time. Also, the user can provide meaningful information such as, e.g., confirmation of classification, and the like.

It should also be appreciated that, according to described embodiments, the importance of color and texture features in classifying polyps can be demonstrated by experiments where polyp classification is treated as a 2-class problem. Consider an experiment where a variety of color-based and texture-based features are used to describe Regions-of-Interest (ROIs), the total number of features is ten (10), with a dimensionality of 585, and the following features are used: 1) Color Layout Descriptor, 2) Edge Histogram Descriptor, 3) Color and Edge Directivity Descriptor, 4) Fuzzy Color and Texture Histogram Descriptor, 5) Gabor filter descriptor, 6) Gray Level Co-Occurrence Matrices (Haralick features), 7) Tamura's texture features, 8) Edge Frequency descriptor, 9) Autocorrelation feature, 10) Primitive length feature.

These ten (10) features are calculated over the ROI using an input image (WL or NIB) and its corresponding binary mask. Three (3) different sets were constructed: a) Feature Set 1 using WL images, b) Feature Set 2 using NIB image, c) Feature Set 3 using a serial concatenation of Feature Set 1 and Feature Set 2 (Feature Set 3=Feature Set 1+Feature Set 2).

The three (3) sets can be classified using a Random-Forest classifier (10-fold cross-validation) on a WEKA software toolbox because it performs better than other common classifiers (i.e. Support Vector Machines, J48).

Tables 1-3 depict the classification results of these experiments:

TABLE 1

Classification Results for Feature Set 1

| | TP Rate | FP Rate | Precision | Recall | F-Measure | ROC Area | Class |
|---|---|---|---|---|---|---|---|
| | 0.706 | 0.483 | 0.623 | 0.706 | 0.662 | 0.664 | Adenoma |
| | 0.517 | 0.294 | 0.608 | 0.517 | 0.559 | 0.664 | Non-Adenoma |
| Weighted Avg. | 0.617 | 0.395 | 0.616 | 0.617 | 0.614 | 0.664 | |

TABLE 2

Classification Results for Feature Set 2

| | TP Rate | FP Rate | Precision | Recall | F-Measure | ROC Area | Class |
|---|---|---|---|---|---|---|---|
| | 0.794 | 0.433 | 0.675 | 0.794 | 0.73 | 0.769 | Adenoma |
| | 0.567 | 0.206 | 0.708 | 0.567 | 0.63 | 0.769 | Non-Adenoma |
| Weighted Avg. | 0.688 | 0.327 | 0.691 | 0.686 | 0.683 | 0.769 | |

TABLE 3

Classification Results for Feature Set

| | TP Rate | FP Rate | Precision | Recall | F-Measure | ROC Area | Class |
|---|---|---|---|---|---|---|---|
| | 0.838 | 0.433 | 0.687 | 0.838 | 0.755 | 0.767 | Adenoma |
| | 0.567 | 0.162 | 0.756 | 0.567 | 0.648 | 0.767 | Non-Adenoma |
| Weighted Avg. | 0.711 | 0.306 | 0.719 | 0.711 | 0.705 | 0.767 | |

This data shows that the WL mode was less accurate than the NIB mode (the ROC areas were 66.4% and 76.9% respectively). This finding is not surprising given the superiority of NIB- over WL-based visual diagnosis by a user, e.g., an endoscopist. Although Feature Set 3 performed similarly to Feature Set 2 (ROC areas 76.7% and 76.9% respectively), the weighted average for Recall over 10-fold cross validation improved by 2.3%, showing that a combination of the two modes could potentially increase overall accuracy. In addition, attribute selection as a preprocessing filtering technique can be performed to reduce the high-dimensionality and evaluate performance.

For attribute selection, a standard correlation-based method can be used and implemented in a WEKA software library (i.e. "CfsSubsetEval"). This essentially estimates the value of a subset of attributes by considering the individual predictive ability of each feature along with the degree of redundancy among the features. Following attribute selection, the feature dimensionality was reduced by 98% on average for each feature set. Tables 4-6 summarize the results of the three (3) feature sets after attribute selection.

TABLE 4

Classification results for Feature Set 1 after attribute selection

|  | TP Rate | FP Rate | Precision | Recall | F-Measure | ROC Area | Class |
|---|---|---|---|---|---|---|---|
|  | 0.706 | 0.417 | 0.658 | 0.706 | 0.681 | 0.718 | Adenoma |
|  | 0.583 | 0.294 | 0.636 | 0.583 | 0.609 | 0.718 | Non-Adenoma |
| Weighted Avg. | 0.648 | 0.359 | 0.648 | 0.648 | 0.647 | 0.718 |  |

TABLE 5

Classification Results for Feature Set 2 after attribute selection

|  | TP Rate | FP Rate | Precision | Recall | F-Measure | ROC Area | Class |
|---|---|---|---|---|---|---|---|
|  | 0.794 | 0.333 | 0.73 | 0.794 | 0.761 | 0.783 | Adenoma |
|  | 0.667 | 0.206 | 0.741 | 0.667 | 0.702 | 0.783 | Non-Adenoma |
| Weighted Avg. | 0.734 | 0.274 | 0.735 | 0.734 | 0.733 | 0.783 |  |

TABLE 6

Classification Results for Feature Set 3 after attribute selection

|  | TP Rate | FP Rate | Precision | Recall | F-Measure | ROC Area | Class |
|---|---|---|---|---|---|---|---|
|  | 0.779 | 0.283 | 0.757 | 0.779 | 0.768 | 0.852 | Adenoma |
|  | 0.717 | 0.221 | 0.741 | 0.717 | 0.729 | 0.852 | Non-Adenoma |
| Weighted Avg. | 0.75 | 0.254 | 0.75 | 0.75 | 0.75 | 0.852 |  |

Tables 4-6 show the significant improvement achieved by attribute selection, with the ROC area increasing across all feature sets, from 1.4% on Feature Set 2 to 8.5% on Feature Set 3, where the ROC reached 85.2%. The selected attributes were investigated and the majority of them were contained in the Color and Edge Directivity and the Fuzzy Color and Texture Histogram descriptors. This observation highlights the importance of combining color, shadows and edge information simultaneously to improve classification.

With the foregoing in mind, according to one implementation of the inventive concepts, classifying polyps is improved by using image transformations and self-similarity indices, which will generate additional features. In the transformation domain, embodiments use discrete wavelet frames, and spatial frequency coefficients from discrete Fourier and cosine image transform.

Furthermore, embodiments compute Fractal Dimension attributes that have shown promise in texture classification applications. A fractal can be defined as a set for which the Hausdorff-Besicovich dimension is strictly greater than the topological dimension. It has been shown that fractal dimension correlates well with a function's roughness. Therefore, embodiments can use fractal dimension to measure the roughness and granularity of the image intensity function. The topological dimension of this function is equal to three (3), consisting of two (2) spatial dimensions plus the intensity.

Embodiments can utilize the method of box counting to compute the fractal dimension explained as follows:

Assuming a fractal structure with dimension D, let $N(\in)$ be the number of non-empty boxes of size ($\in$) required to cover the fractal support. Using the relation $N(\in) \approx \in^{-D}$, embodiments can numerically estimate D from $$D = \lim_{r \to 0} \frac{\log N(\in)}{-\log \in}$$

by least squares fitting.

For the case of grayscale images or continuous functions, embodiments can generate eight (8) binary sets using multiple Otsu thresholding, then compute the fractal dimension, area, and mean intensity for each point set. The latter measurements can be added to the texture feature set.

The second group of features can be computed from discrete wavelet frames. To produce the wavelet frame representation, embodiments can compute the discrete wavelet transform for all possible signal translations at multiple scales.

Embodiments can then form a N—componentvector, where N is the number of sub-bands and N=1+3I and I denotes the depth of wavelet decomposition. Embodiments the compute energy signatures and average them over the ROI. Furthermore, embodiments can compute spatial frequency transformations for texture representation. Embodiments can also utilize Discrete Fourier Transform magnitude and the Discrete Cosine Transform coefficients to capture the spectral properties of texture. For example, fine texture has greater high frequency components, whereas coarse texture is represented by lower frequencies. It is worth noting that these orthogonal basis vector representations may be used in a sparse coding scheme for visual reconstruction.

A focus of the inventive concepts is on tests that indicate if described embodiments increase the predictive capability for Adenomas. Therefore, for such tests, Feature Set 3 can be used as a baseline to train and test a support vector machine-based classifier for classification of polyp data into non-adenomas and adenomas.

Embodiments can also use a 10-fold cross-validation and the Area Under the ROC to evaluate the classifier performance. Embodiments can use the Random Forest classification with the same correlation-based method that was used on Feature Set 3, to facilitate comparisons with results shown in Table 6:

TABLE 6

Classification Results for Feature Set 3 after attribute selection

| | TP Rate | FP Rate | Precision | Recall | F-Measure | ROC Area | Class |
|---|---|---|---|---|---|---|---|
| | 0.779 | 0.283 | 0.757 | 0.779 | 0.768 | 0.852 | Adenoma |
| | 0.717 | 0.221 | 0.741 | 0.717 | 0.729 | 0.852 | Non-Adenoma |
| Weighted Avg. | 0.75 | 0.254 | 0.75 | 0.75 | 0.75 | 0.852 | |

Embodiments can then compute Wavelet, Discrete Cosine, Discrete Fourier, and Fractal Dimension features and concatenate them to Feature Set 3, to form the new Feature Set 4. The results are shown in Table 7:

TABLE 7

Classification Results for Feature Set 4 after attribute selection

| | TP Rate | FP Rate | Precision | Recall | F-Measure | ROC Area | Class |
|---|---|---|---|---|---|---|---|
| | 0.882 | 0.200 | 0.833 | 0.882 | 0.857 | 0.903 | Adenoma |
| | 0.800 | 0.118 | 0.857 | 0.800 | 0.828 | 0.903 | Non-Adenoma |
| Weighted Avg. | 0.844 | 0.161 | 0.844 | 0.844 | 0.843 | 0.903 | |

From the foregoing it is observed that the introduction of frequency domain and fractal features reported in Table 7 improved the classification performance of the baseline detector reported in Table 6 by 5.1%. These results hold the promise of further improvement of the classification performance if the system is paired with subspace learning techniques and classification models.

Although an example processing system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as software for performing described functions (FIGS. 1-5), can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server (e.g., forming a portion of system 100) is a general purpose computer, and sometimes it is a custom-tailored special purpose electronic device, and sometimes it is a combination of these things.

Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

Other implementations are within the scope of the following claims. For example, although examples have been described in which the information received and analyzed by the system is used for determining security characteristics of an entity, the results of the analysis provide useful information about the entity that could be used for a variety other purposes and in other ways.

The invention claimed is:

1. A system for classifying polyps, the system comprising:
a polyp imaging engine, the polyp imaging engine configured to:
generate, from images of at least one polyp taken from different perspectives, a new polyp image, the new polyp image having fewer reflection artifacts and occlusions than the images of the at least one polyp taken from different perspectives, and
compute, based on the generated new polyp image, a polyp surface model; and
a learning engine, the learning engine configured to:
apply linear subspace learning techniques and nonlinear subspace learning techniques to identify discriminate features in the polyp surface model, and
classify the at least one polyp based on the identified discriminate features.

2. The system of claim 1, wherein classifying the at least one polyp based on the identified discriminate features includes classifying the at least one polyp as adenomatous or hyperplastic.

3. The system of claim 1, further comprising a polyp image database comprising images of a plurality of polyps taken from different perspectives, wherein the at least one polyp is included in the plurality of polyps.

4. The system of claim 3, wherein at least one of the images of the plurality of polyps taken from different perspectives includes images generated using Narrow Band Imaging (NBI).

5. The system of claim 4 wherein generating the images of the plurality of polyps taken from different perspectives using NBI comprises:
generating a first image of at least one of the plurality of polyps using a light source emitting at or about 415 nanometers, and
generating a second image of the at least one of the plurality of polyps using a light source emitting at or about 540 nanometers.

6. The system of claim 3, wherein at least one of the images of the plurality of polyps taken from different perspectives comprises images generated using a white light (WL) source.

7. The system of claim 1, wherein applying subspace learning techniques to identify discriminate features in the polyp surface model comprises:
developing sparse representations of the polyp to build polyp representations that are not affected by imagine artifacts and occlusions.

8. The system of claim 7, wherein the developed sparse representations are utilized to:
estimate accurate decision functions and separation between statistical prototype of adenomas and non-adenomas polyps.

9. The system of claim 1 wherein the polyp imaging engine is further configured to:
generate color and texture data for images of the at least one polyp taken from different perspectives.

10. A method for classifying polyps, the method comprising:
generating, from images of at least one polyp taken from different perspectives, a new polyp image, the new polyp image having fewer reflection artifacts and occlusions than the images of the at least one polyp taken from different perspectives;
computing, based on the generated new polyp image, a polyp surface model; and
applying, by a learning engine, a linear subspace learning techniques and nonlinear subspace learning techniques to identify discriminate features in the polyp surface model, and
classifying the at least one polyp based on the identified discriminate features.

11. The method of claim 10, wherein classifying the at least one polyp based on the identified discriminate features includes classifying the at least one polyp as adenomatous or hyperplastic.

12. The method of claim 10, further comprising:
storing, in an image database, images of a plurality of polyps taken from different perspectives, wherein the at least one polyp is included in the plurality of polyps.

13. The method of claim 12, further comprising:
generating at least one of the images of the plurality of polyps taken from different perspective using Narrow Band Imaging (NBI).

14. The method of claim 13, wherein generating the images of the plurality of polyps taken from different perspectives using NBI comprises:
generating a first image of at least one of the plurality of polyps using a light source emitting at or about 415 nanometers, and
generating a second image of the at least one of the plurality of polyps using a light source emitting at or about 540 nanometers.

15. The method of claim 12, wherein at least one of the images of the plurality of polyps taken from different perspectives comprises images generated using a white light (WL) source.

16. The method of claim 10, further comprising:
developing sparse representations of the at least one polyp to build polyp representations that are not affected by imagine artifacts and occlusions.

17. The method of claim 16, further comprising:
estimating accurate decision functions and separation between statistical prototype of adenomas and non-adenomas polyps.

18. The method of claim 10, further comprising:
generating color and texture data for the images of the at least one polyp taken from different perspectives.

* * * * *